(12) United States Patent
Asirvatham (10) Patent No.: US 12,274,883 B2
(45) Date of Patent: Apr. 15, 2025

(54) METHODS AND SYSTEMS FOR ELECTROPORATION

(71) Applicant: Mayo Foundation for Medical Education and Research, Rochester, MN (US)

(72) Inventor: Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 42 days.

(21) Appl. No.: 18/091,954

(22) Filed: Dec. 30, 2022

(65) Prior Publication Data
US 2023/0149718 A1 May 18, 2023

Related U.S. Application Data

(62) Division of application No. 16/763,712, filed as application No. PCT/US2018/064914 on Dec. 11, 2018, now Pat. No. 11,541,241.

(60) Provisional application No. 62/597,007, filed on Dec. 11, 2017.

(51) Int. Cl.
| | |
|---|---|
| A61N 1/36 | (2006.01) |
| A61B 5/283 | (2021.01) |
| A61B 5/316 | (2021.01) |
| A61N 1/05 | (2006.01) |
| A61N 1/365 | (2006.01) |
| A61B 18/00 | (2006.01) |
| A61B 18/12 | (2006.01) |
| A61N 1/32 | (2006.01) |

(52) U.S. Cl.
CPC .......... *A61N 1/36507* (2013.01); *A61B 5/283* (2021.01); *A61B 5/316* (2021.01); *A61N 1/056* (2013.01); *A61B 2018/00351* (2013.01); *A61B 2018/00613* (2013.01); *A61B 2018/00839* (2013.01); *A61B 18/12* (2013.01); *A61N 1/327* (2013.01)

(58) Field of Classification Search
CPC .......................... A61N 1/36507; A61B 5/316
USPC ......................................................... 607/62
See application file for complete search history.

(56) References Cited

U.S. PATENT DOCUMENTS

| | | |
|---|---|---|
| 4,166,113 A | 8/1979 | Norton et al. |
| 4,819,751 A | 4/1989 | Shimada et al. |

(Continued)

FOREIGN PATENT DOCUMENTS

| | | |
|---|---|---|
| CA | 2158051 | 9/1994 |
| WO | WO 2011/159641 | 12/2011 |

(Continued)

OTHER PUBLICATIONS

Boyden et al., "Cardiac Purkinje fibers and arrhythmias; The GK Moe Award Lecture 2015," Hearth Rhythm, May 2016, 13(5):1172-1181.

(Continued)

*Primary Examiner* — Nicole F Lavert
(74) *Attorney, Agent, or Firm* — Fish & Richardson P.C.

(57) ABSTRACT

This document describes methods and materials for improving the delivery of electroporation. For example, this document describes methods and devices for delivering electroporation while mitigating risks of ventricular fibrillation.

19 Claims, 2 Drawing Sheets

(56) References Cited

U.S. PATENT DOCUMENTS

| | | | |
|---|---|---|---|
| 5,640,967 A * | 6/1997 | Fine | G16H 40/63 |
| | | | 600/301 |
| 5,860,974 A | 1/1999 | Abele | |
| 6,023,638 A | 2/2000 | Swanson | |
| 6,086,582 A | 7/2000 | Altman et al. | |
| 7,190,997 B1 | 3/2007 | Darvish et al. | |
| 7,736,346 B2 | 6/2010 | Miller et al. | |
| 8,036,741 B2 | 10/2011 | Jahns et al. | |
| 11,541,241 B2 | 1/2023 | Asirvatham | |
| 11,969,197 B2 | 4/2024 | DeSimone et al. | |
| 12,076,070 B2 * | 9/2024 | Forsyth | A61B 18/12 |
| 2001/0041890 A1 | 11/2001 | Hassett et al. | |
| 2002/0151812 A1 | 10/2002 | Scheiner et al. | |
| 2009/0099560 A1 | 4/2009 | Rioux et al. | |
| 2011/0144028 A1 | 6/2011 | Sharma | |
| 2012/0143099 A1 | 6/2012 | Daniels et al. | |
| 2013/0066315 A1 | 3/2013 | Subramaniam et al. | |
| 2013/0253616 A1 | 9/2013 | Libbus et al. | |
| 2014/0081111 A1 | 3/2014 | Tun et al. | |
| 2015/0132409 A1 | 5/2015 | Stein et al. | |
| 2016/0051324 A1 | 2/2016 | Stewart et al. | |
| 2016/0058504 A1 | 3/2016 | Davies et al. | |
| 2016/0113586 A1 * | 4/2016 | Hemming | A61B 5/316 |
| | | | 600/300 |
| 2016/0113709 A1 | 4/2016 | Maor | |
| 2016/0249978 A1 | 9/2016 | Lee et al. | |
| 2016/0270845 A1 | 9/2016 | Benscoter et al. | |
| 2016/0310211 A1 | 10/2016 | Long | |
| 2017/0035499 A1 * | 2/2017 | Stewart et al. | A61N 1/327 |
| 2017/0042614 A1 | 2/2017 | Salahieh et al. | |
| 2017/0065339 A1 | 3/2017 | Mickelsen | |
| 2017/0105793 A1 | 4/2017 | Cao et al. | |
| 2017/0189097 A1 * | 7/2017 | Viswanathan | A61N 1/0587 |
| 2017/0340888 A1 | 11/2017 | Callas et al. | |
| 2018/0085159 A1 | 3/2018 | Sulkin et al. | |
| 2018/0214196 A1 | 8/2018 | Eum et al. | |
| 2019/0105057 A1 | 4/2019 | Radl et al. | |
| 2020/0205890 A1 | 7/2020 | Harlev et al. | |
| 2020/0298008 A1 | 9/2020 | Asirvatham | |
| 2020/0305946 A1 | 10/2020 | DeSimone et al. | |

FOREIGN PATENT DOCUMENTS

| | | |
|---|---|---|
| WO | WO 2014/143898 | 9/2014 |
| WO | WO 2014/195933 | 12/2014 |
| WO | WO 2017/062753 | 4/2017 |
| WO | WO 2017/074920 | 5/2017 |

OTHER PUBLICATIONS

Damiano Jr. et al., "The effect of chemical ablation of the endocardium on ventricular fibrillation threshold," Circulation, Sep. 1986, 74(3):645-652.

DeSimone et al., "Novel balloon catheter device with pacing, ablating, electroporation, and drug-eluting capabilities for atrial fibrillation treatment—preliminary efficacy and safety studies in a canine model," Transl. Res., Dec. 2014, 164(6):508-514.

Evans Jr. et al., "Predictors of in-hospital mortality after DC catheter ablation of atrioventricular junction. Results of a prospective, international, multicenter study," Circulation, Nov. 1991, 84(5):1924-1937.

Frühling et al., "Single-center nonrandomized clinical trial to assess the safety and efficacy of irreversible electroporation (IRE) ablation of liver tumors in humans: Short to mid-term results," Eur. J. Surg. Oncology, Apr. 2017, 43(4):751-757.

Haïssaguerre et al., "Mapping and ablation of idiopathic ventricular fibrillation," Circulation, Aug. 2002, 106(8):962-967.

Haïssaguerre et al., "Role of Purkinje conducting system in triggering of idiopathic ventricular fibrillation," Lancet, Feb. 2002, 359(9307):677-678.

Hou et al., "Determination of ventricular vulnerable period and ventricular fibrillation threshold by use of T-wave shocks in patients undergoing implantation of cardioverter/defibrillators," Circulation, Nov. 1, 1995, 92(9):2558-2564.

Hwang et al., "Upper limit of vulnerability reliably predicts the defibrillation threshold in humans," Circulation, Nov. 1994, 90(5):2308-2314.

International Preliminary Report on Patentability in International Application No. PCT/US2018/064914 dated Jun. 25, 2020, 9 pages.

International Search Report & Written Opinion in International Application No. PCT/US2018/064914 dated Feb. 27, 2019, 15 pages.

Knecht et al., "Long-term follow-up of idiopathic ventricular fibrillation ablation: a multicenter study," J. Am. Coll. Cardiology, Aug. 4, 2009, 54(6):522-528.

Lemery et al., "Low energy direct current ablation in patients with the Wolff-Parkinson-White syndrome: clinical outcome according to accessory pathway location," Pacing Clin. Electrophysiology, Nov. 1991, 14(11 Pt 2):1951-1955.

Livia et al., "Electroporative Elimination of Purkinje Fibers Reduces Vulnerability to Ventricular Fibrillation," Presented at Heart Rhythm Society, May 11-12, 2017, 1 page.

Lopera et al., "Identification and ablation of three types of ventricular tachycardia involving the his-purkinje system in patients with heart disease," J. Cardiovasc. Electrophysiol., 2004, 15(1):52-58.

Minners et al., "Dinitrophenol, cyclosporin A, and trimetazidine modulate preconditioning in the isolated rat heart: support for a mitochondrial role in cardioprotection," Cardiovasc. Research, Jul. 2000, 47(1):68-73.

Neven et al., "Epicardial linear electroporation ablation and lesion size," Heart Rhythm, Aug. 2014, 11(8):1465-1470.

Nogami et al., "Mapping and ablation of idiopathic ventricular fibrillation from the Purkinje system," Heart Rhythm, 2005, 2(6):646-649.

Odening et al., "Electro-Mechanical Remodeling in Transgenig Short QT Syndrome Rabbits," Poster C-PO04-01:S327, Heart Rhythm Society in May 11-12, 2017, 1 page.

O'Nénáin et al., "Catheter ablation by low energy DC shocks for successful management of atrial flutter," Br. Heart Journal, Jan. 1992, 67(1):67-71.

Santoro et al., "Ventricular fibrillation triggered by PVCs from papillary muscles: clinical features and ablation," J. Cardiovasc. Electrophysiology, Nov. 2014, 25(11):1158-1164.

Sutter et al., "Safety and Efficacy of Irreversible Electroporation for the Treatment of Hepatocellular Carcinoma Not Amenable to Thermal Ablation Techniques: A Retrospective Single-Center Case Series," Radiology, Sep. 2017, 284(3):877-886.

Swerdlow et al., "Comparative reproducibility of defibrillation threshold and upper limit of vulnerability," Pacing Clin. Electrophysiology, Dec. 1996, 19(12 Pt 1):2103-2111.

Valerio et al., "Nanoknife Electroporation Ablation Trial: A Prospective Development Study Investigating Focal Irreversible Electroporation for Localized Prostate Cancer," J. Urology, Mar. 2017, 197(3 Pt 1):647-654.

van Driel et al., "Pulmonary vein stenosis after catheter ablation: electroporation versus radiofrequency," Circ. Arrhythm. Electrophysiology, Aug. 2014, 7(4):734-738.

Vogel et al., "Induction Chemotherapy Followed by Resection or Irreversible Electroporation in Locally Advanced Pancreatic Cancer (IMPALA): A Prospective Cohort Study," Ann. Surg. Oncology, Sep. 2017, 24(9):2734-2743.

Witt et al., "Electroporative Myocardial Ablation Utilizing a Non-contact, Virtual Electrode: Proof of Concept in Ex-vivo and In-vivo Canine Hearts," Poster, Presented at Heart Rhythm Society, May 11-12, 2017, 1 page.

Witt et al., "Electroporative Myocardial Ablation Utilizing a Non-contact, Virtual Electrode: Proof of Concept in Ex-vivo and In-vivo Canine Hearts," Presented at Heart Rhythm Society in May 11-12, 2017, 14(5):S327-S417.

Wittkampf et al., "Myocardial lesion depth with circular electroporation ablation," Circ. Arrhythm. Electrophysiology, Jun. 1, 2012, 5(3):581-586.

(56) References Cited

OTHER PUBLICATIONS

Yeh et al., "Simplified Method for Concentration of Mitochondrial Membrane Protein Complexes," Electrophoresis, Jun. 2010, 31(12):1934-1936.
U.S. Appl. No. 16/754,935, filed Apr. 9, 2020, Christopher V. DeSimone, Published as U.S. Patent Application Publication No. 2020/0305946.
Chen et al., "Comparison of the defibrillation threshold and the upper limit of ventricular vulnerability," Circulation, May 1986, 73(5):1022-1028.
Kleinhaus et al., "The effects on canine cardiac Purkinje fibers of Chrysaora quinquecirrha (sea nettle) toxin," Toxicon, Jul. 1973, 11(4):341-349.
Livia et al., "Abstract #: C-PO04-139: Electroporative Elimination of Purkinje Fibers Reduces Vulnerability to Ventricular Fibrillation," Heart Rhythm, May 2017, 14(5):S327-S417.
Livia et al., "Elimination of Purkinje Fibers by Electroporation Reduces Ventricular Fibrillation Vulnerability," J. Am. Heart Assoc., Aug. 2018, 7(15):e009070, 9 pages.
McLeod et al., "Delayed ischemic preconditioning activates nuclear-encoded electron-transfer chain gene expression in parallel with enhanced postanoxic mitochondrial respiratory recovery," Circulation, Aug. 2004, 110:534-539.
Spiro et al., "Use of left ventricular support devices during acute coronary syndrome and percutaneous coronary intervention," Curr. Cardiol. Rep., Dec. 2014, 16(12):544.

\* cited by examiner

METHODS AND SYSTEMS FOR ELECTROPORATION

CROSS-REFERENCE TO RELATED APPLICATIONS

This application is a Division of U.S. application Ser. No. 16/763,712, filed on May 13, 2020, which is a National Stage Application under 35 U.S.C. § 371 of International Application No. PCT/US2018/064914, having an International Filing Date of Dec. 11, 2018, which priority to U.S. Application Ser. No. 62/597,007, filed on Dec. 11, 2017. The disclosure of the prior application is considered part of the disclosure of this application, and is incorporated in its entirety into this application.

BACKGROUND

1. Technical Field

This document relates to methods and materials for delivering electroporation. For example, this document relates to methods and devices for delivering cardiac electroporation while mitigating risks of ventricular fibrillation.

2. Background Information

Sudden cardiac death is a leading cause of mortality, the majority of which is due to ventricular fibrillation. Further, ventricular fibrillation is the most common terminal arrhythmia in humans. Occurring either as a primary event or secondary event to concomitant cardiac and non-cardiac diseases and events, prevention of this arrhythmia remains rudimentary. Although defibrillators and anti-arrhythmics provide an element of protection in select cases, sudden cardiac death remains a major worldwide health problem.

Electroporation is a technique that uses a high voltage, rapid burst of current to non-thermally introduce multiple nano-pores within the cells' walls of surrounding tissue, specifically within the lipid bilayer of the cell membranes as a result of the electrical field. Depending on the voltage and frequency used, these pores can be reversible (i.e., increase the permeability of these cell to chemotherapeutic agents) and/or irreversible (i.e., trigger cell death by the process of apoptosis rather than necrosis). Given the different composition of each cell-type membrane, along with other discrepancies, electroporation can allow for a differential effect on different tissues.

A unique challenge with cardiac electroporation, including tumor and other electroporation when done near or around the heart, is there is a need for accurate timing of energy delivery to avoid the life-threatening possibility of creating arrhythmia from delivering electroporation-direct current energy during the vulnerable period of cardiac activation and creating ventricular fibrillation and other arrhythmias.

SUMMARY

This document describes methods and materials for the delivery of electroporation. For example, this document describes methods and devices for delivering electroporation while mitigating risks of ventricular fibrillation.

In one aspect, this disclosure is directed to a method of delivering electroporation. The method can include placing a lead comprising a first electrode in a heart of a patient, measuring cardiac signals from the first electrode on the lead in the heart, and delivering stimulation to the heart via the first electrode. In some cases, measuring cardiac signals can include measuring a first electrocardiogram between the first electrode and a second electrode of the lead, where the first electrode and the second electrode are located linearly along the lead. In some cases, measuring cardiac signals can include measuring a second electrocardiogram between the first electrode and a third electrode of the lead, where the first electrode and the third electrode are located linearly along the lead. In some cases, measuring cardiac signals can also include comparing the first electrocardiogram and the second electrocardiogram, and removing signals common to the first electrocardiogram and the second electrocardiogram, creating a filtered electrocardiogram. In some cases, the method can also include triggering the delivery of stimulation based on the filtered electrocardiogram.

In some cases, delivering stimulation can further include delivering a first set of stimulation pulses for a cardiac cycle, where the first set of stimulation pulses has a first intensity below a threshold. In some cases, measuring cardiac signals can also include detecting a summation in a portion of an electrocardiogram of the cardiac cycle. In some cases, the delivering stimulation can also include delivering a second set of stimulation pulses for the cardiac cycle, where the second set of stimulation pulses has a second intensity above the threshold. In some cases, delivering stimulation can include inhibiting stimulation during the portion of the cardiac cycle when summation is detected. In some cases, delivering stimulation can also include delivering a third set of stimulation pulses for the cardiac cycle, where the third set of stimulation pulses has a third intensity between the first intensity and the threshold. In some cases, measuring cardiac signals can include detecting a second summation in a second portion of a second electrocardiogram of the cardiac cycle. In some cases, delivering stimulation can also include delivering a fourth set of stimulation pulses for the cardiac cycle when summation is not detected, where the fourth set of stimulation pulses has a fourth intensity above the threshold.

In another aspect, the disclosure is related to a method of triggering electroporation. The method can include measuring a first electrocardiogram between a first electrode and a second electrode of a lead, where the first electrode and the second electrode are located linearly along the lead, measuring a second electrocardiogram between the first electrode and a third electrode of the lead, where the first electrode and the third electrode are located linearly along the lead, comparing the first electrocardiogram and the second electrocardiogram, removing signals common to the first electrocardiogram and the second electrocardiogram, creating a filtered electrocardiogram, and triggering electroporation stimulation based on the filtered electrocardiogram. In some cases, the method can also include delivering stimulation to a heart. In some cases, delivering stimulation can include delivering a first set of stimulation pulses for a cardiac cycle, where the first set of stimulation pulses has a first intensity below a threshold. In some cases, measuring cardiac signals can include detecting a summation in a portion of an electrocardiogram of the cardiac cycle. In some cases, delivering stimulation can include delivering a second set of stimulation pulses for the cardiac cycle, where the second set of stimulation pulses has a second intensity above the threshold. In some cases, delivering stimulation can include inhibiting stimulation during the portion of the cardiac cycle when summation is detected. In some cases, delivering stimulation can also include delivering a third set of stimulation pulses for the cardiac cycle, where the third set of stimulation pulses has a third intensity between the first intensity and the threshold. In some cases, measuring cardiac signals can also include detecting a second summation in a second portion of a second electrocardiogram of the cardiac cycle. In some cases, delivering stimulation can further include delivering a fourth set of stimulation pulses for the cardiac cycle when summation is not detected, where the fourth set of stimulation pulses has a fourth intensity above the threshold.

In yet another aspect, the disclosure relates to a device for delivering electroporation. The device can include a lead including a first electrode, a second electrode, and a third electrode, where the electrodes are positioned linearly along a length of the lead, a memory that is capable of storing computer executable instructions, and a processor that is configured to facilitate execution of the executable instructions stored in memory. The instructions can cause the processor to measure cardiac signals from the first electrode on the lead, and generate stimulation. In some cases, measuring cardiac signals can include measuring a first electrocardiogram between the first electrode and the second electrode. In some cases, measuring cardiac signals can also include measuring a second electrocardiogram between the first electrode and the third electrode. In some cases, measuring cardiac signals can further include comparing the first electrocardiogram and the second electrocardiogram, and removing signals common to the first electrocardiogram and the second electrocardiogram, creating a filtered electrocardiogram. In some cases, the instructions can cause the processor to trigger the generation of stimulation based on the filtered electrocardiogram.

In some cases, generating stimulation can include generating a first set of stimulation pulses for a cardiac cycle, where the first set of stimulation pulses has a first intensity below a threshold. In some cases, measuring cardiac signals can include detecting a summation in a portion of an electrocardiogram of the cardiac cycle. In some cases, generating stimulation can further include generating a second set of stimulation pulses for the cardiac cycle, where the second set of stimulation pulses has a second intensity above the threshold. In some cases, generating stimulation can include inhibiting stimulation generation during the portion of the cardiac cycle when summation is detected. In some cases, generating stimulation can also include generating a third set of stimulation pulses for the cardiac cycle, where the third set of stimulation pulses has a third intensity between the first intensity and the threshold. In some cases, measuring cardiac signals can further include detecting a second summation in a second portion of a second electrocardiogram of the cardiac cycle. In some cases, generating stimulation can include generating a fourth set of stimulation pulses for the cardiac cycle when summation is not detected, where the fourth set of stimulation pulses has a fourth intensity above the threshold.

Particular embodiments of the subject matter described in this document can be implemented to realize one or more of the following advantages. The methods and systems described herein can reduce the risk of a patient entering ventricular fibrillation during delivery of cardiac electroporation. Therapeutic levels of electroporation can be delivered for a greater portion of a cardiac cycle when using the systems and methods provided herein. This can advantageously reduce the amount of time an electroporation procedure takes to complete. Using the methods and systems provided herein, efficacy and safety can be increased for cardiac electroporation, and electroporation for other electrical systems (e.g., brain, nerves, GI tract, etc.). Additionally, abnormal arrhythmias can be diagnosed with the systems and methods provided herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods and examples are illustrative only and not intended to be limiting.

The details of one or more embodiments of the invention are set forth in the accompanying drawings and the description below. Other features, objects, and advantages of the invention will be apparent from the description, drawings, and from the claims.

DESCRIPTION OF DRAWINGS

Like reference numbers represent corresponding parts throughout.

DETAILED DESCRIPTION

This document describes methods and materials for improving the delivery of electroporation. For example, this document describes methods and devices for delivering electroporation while mitigating risks of ventricular fibrillation.

Ventricular fibrillation is the most common terminal arrhythmia in humans and electroporation is a technique that uses a high voltage rapid burst of current to non-thermally introduce multiple nano-pores within the cells' walls of surrounding tissue, specifically within the lipid bilayer of the cell membranes as a result of the electrical field. A unique challenge with cardiac electroporation, including tumor and other types of electroporation when done near or around the heart, is there is a need for accurate timing of energy delivery to avoid the life-threatening possibility of creating arrhythmia, especially during the vulnerable period of cardiac activation.

Present techniques to avoid inducing ventricular fibrillation are not complete, specifically using the electrocardiogram and points of reference on the QRS inscription of the ECG. However, for cardiac applications, the QRS can vary, cardiac rates can vary, and since the electroporation is being delivered directly on the heart (rather than a tumor material nearby), a slight error can give rise to malignant arrhythmia. Because the electrical therapy of electroporation can interfere with the inherent electrical activity of the heart, if electroporation is delivered randomly, there is a one in twenty risk that a single pulse can induce a fatal ventricular fibrillation. Specifically, there can be periods in the heart cycle known as vulnerable periods, and if stimulation is delivered during these vulnerable periods, a ventricular fibrillation can be induced. In some cases, it can be difficult to resuscitate a patient after such an occurrence.

In some cases, to avoid providing stimulation in the vulnerable period, an ECG can be used to measure the cardiac cycle and triggers stimulation after the QRS, such as during the t-wave. However, triggering stimulation following the QRS of a patient is problematic because the reason for delivering electroporation is that a problem has been identified with the QRS of the patient. The problems in the QRS of the patient can lead to inaccurate delivery of electroporation. Further, when delivering electroporation only after the QRS, therapy can only be delivered during a small portion of the cardiac cycle, and accordingly, stimulation may be front loaded to give high levels of stimulation in short periods of time. This can cause stimulation to be painful for nerves, muscles, or other body parts, and therefore, the patient may need general anesthesia during therapy.

The methods and systems described herein can provide electroporation with increased safety and efficacy, while reducing the amount of time taken to complete the procedure and the risk of a patient entering ventricular fibrillation during the procedure.

Figure 1:
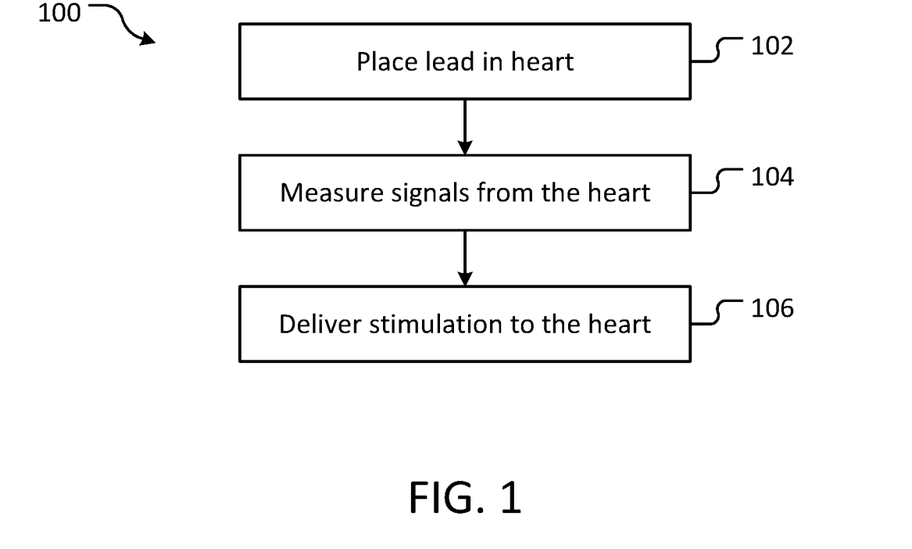
FIG. 1 is a flow chart of a first method of delivering electroporation, in accordance with some embodiments provided herein.

Referring to FIG. 1, an example method 100 of delivering electroporation can include placing a lead in a patient's heart at 102, measuring signals from the heart at 104, and delivering stimulation to the heart at 106.

Placing a lead at 102 can include placing a lead in or around the heart (e.g. an atrium and/or a ventricle). The lead can include multiple electrodes (e.g., 3-6 electrodes). In some cases, the electrodes are linearly spaced along the lead. The lead can be a screw in lead, or other type of lead. In some cases, the electrodes can vary in size. For example, electrodes that are more distal can be smaller than electrodes that are more proximal. In some cases, a ring electrode can have 1.5 to 4 times the surface area of other electrodes. In some cases, a proximal electrode can have a width 1.5 to 3 times the width of a distal electrode. In some cases, the electrodes can be both sensing and delivering electrodes. In some cases, multiple leads and/or electrodes may be implanted such that one set of electrodes (e.g., on one lead) can provide sensing, while another set of electrodes (e.g., on a second lead) can provide electroporation through electrical stimulation. In some cases, an electrode spaced farther away than other electrodes may be used as a return electrode, thereby increasing the area covered during bipolar electroporation. Further, by placing the electrodes in or around the heart, the electrodes can be more reliable than surface electrodes in determining vulnerable periods.

Measuring signals from the heart at 104 can include measuring signals from the electrodes on the lead placed in or around the heart. However, local electrodes can pick up external noise from various devices (e.g., from generators, pumps, warmers, or other external or internal devices). These devices can have leakage currents that can be picked up by the electrodes in the heart. This can be problematic as algorithms that use intracardiac electrograms, such as ventricular electrograms, can be thrown off by the noise measured from other devices, which can lead to error in determining when to deliver stimulation. The signals measured from the heart at 104 can be used to determine when to trigger and/or deliver stimulation. Methods for measuring signals from the heart and triggering stimulation are described in more detail with respect to FIG. 2.

Delivering stimulation to the heart at 106 can include using the electrodes on the lead placed in and/or around the heart to deliver stimulation. Methods of delivering stimulation are described in more detail with respect to FIGS. 3 and 4.

Figure 2:
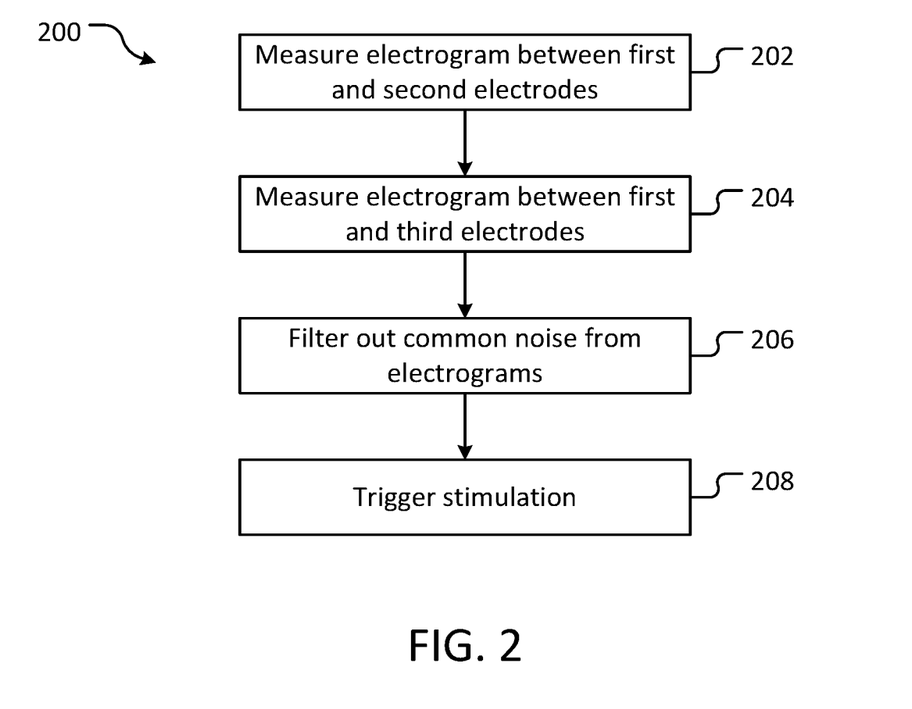
FIG. 2 is a flow chart of a method of triggering electroporation, in accordance with some embodiments provided herein.

Referring to FIG. 2, an example method 200 of triggering electroporation can include measuring a first electrogram between a first electrode and a second electrode at 202, measuring a second electrogram between a first electrode and a third electrode at 204, filtering out common noise from the first and second electrograms at 206, and triggering stimulation at 208.

Measuring a first electrogram between a first electrode and a second electrode at 202 can include measuring an electrogram between two closely spaced electrodes. In some cases, these electrodes can the two most distally located electrodes on the lead (e.g., electrodes 1 and 2).

Measuring a second electrogram between a first electrode and a third electrode at 204 can include measuring an electrogram between two electrodes spaced farther apart than the electrodes used to measure the first electrogram. In some cases, these electrodes can be a most distally located electrode and an electrode more proximal than the second electrode used to measure the first electrogram (e.g., electrodes 1 and 3, or electrodes 1 and 4).

Filtering out common noise from the first and second electrograms at 206 can include comparing the first and second electrograms measured at 202 and 204. A common mode rejection filter can be used to remove signals common to both electrograms. Even small changes in distances between electrodes placed in or around the heart can lead to large differences in electrogram signals, accordingly, signals that are common between the electrograms are likely caused by leakage from other devices near the heart. Once the common signals between the electrograms are removed, a modified electrogram can be used to determine when to trigger electrical stimulation.

Triggering stimulation at 208 can include triggering electrical stimulation after a cardiac signal is sensed in the modified electrogram. The electrical stimulation can be deliver immediately after the cardiac signal. Alternatively, or in addition, the electrical stimulation can be delivered for up to about 80 ms after the sensed cardiac signal. In some cases, this period of time is known as the absolute refractory period, and can reduce the chance of inducing ventricular fibrillation.

The vulnerable period can be narrow (e.g., 45-50 ms) with respect to an entire cardiac cycle, and is during cardiac repolarization and giving any significant energy that would cause depolarization of heart cells can induce ventricular fibrillation.

Figure 3:
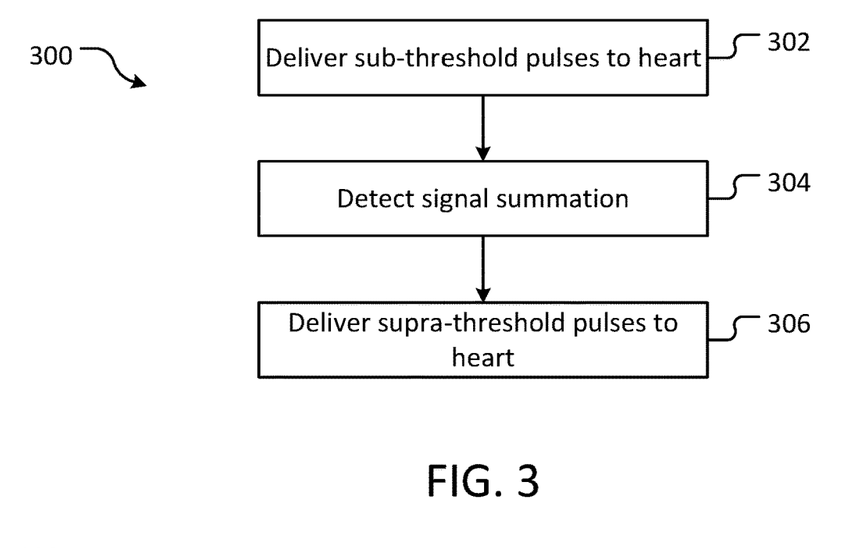
FIG. 3 is a flow chart of a second method of delivering electroporation, in accordance with some embodiments provided herein.

Referring to FIG. 3, another example method 300 of delivering electroporation can include delivering sub-threshold pulses to the heart at 302, detecting signal summation at 304, and delivering supra-threshold pulses to the heart at 306. This method can be used to increase the period of time in which stimulation therapy can be delivered without substantially increasing the risk of ventricular fibrillation.

Delivering sub-threshold pulses to the heart at 302 can include delivering stimulation below a therapeutic threshold throughout a cardiac cycle. In some cases, sub-threshold stimulation can be delivered as a plurality of pulses. Sub-threshold stimulation can be delivered with a voltage of about 10 microvolts to about 100 microvolts. The sub-threshold stimulation can be delivered between two electrodes of the lead (e.g., electrodes 1 and 3). When the cardiac cycle is in the refractory period, this sub-threshold stimulation will have little effect on the cardiac signals measured in the electrogram. However, when sub-threshold stimulation is delivered in the relative refractory period, there may be small changes seen in the cardiac signal.

In addition, delivering sub-threshold stimulation during the vulnerable period, a summation can be seen in the cardiac signal measured on the electrogram. Detecting signal summation at 304 can identify the vulnerable period of a cardiac cycle. In some cases, the cardiac signal can be measured between two electrodes (e.g., electrodes 2 and 4). In some cases, multiple electrograms can be measured, as described in FIG. 2, and compared to determine a more accurate electrogram. By identifying the vulnerable period, therapy can be delivered to avoid the vulnerable period. This can increase safety and efficacy.

Delivering supra-threshold pulses to the heart at 306 can include delivering therapeutic stimulation to substantially all of a cardiac cycle, except for the vulnerable period. Supra-threshold pulses can have a pulse width (e.g., 100 ns-3 ms). In some cases, the supra-threshold pulses can have varying pulse widths. Supra-threshold pulses can have an amplitude of 1 V to 4 kV. By delivering the supra-threshold pulses for a greater portion of the cardiac cycle, the length of the overall procedure can be reduced. In some cases, the electroporation procedure can take 350-400 ms.

Figure 4:
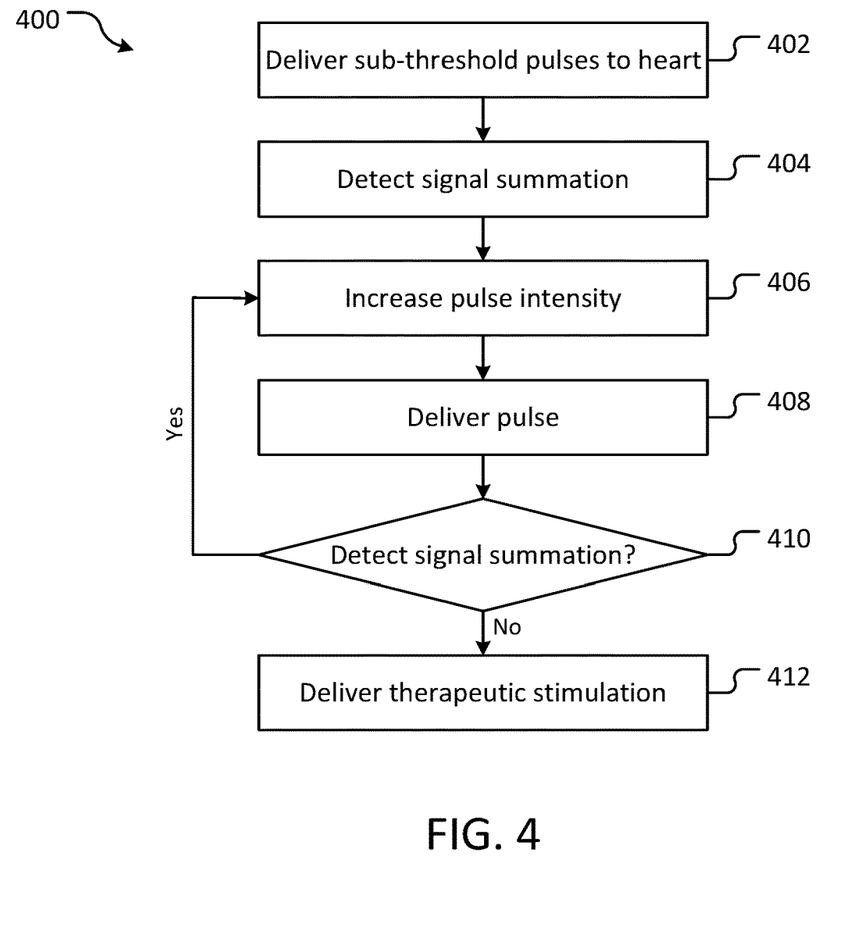
FIG. 4 is a flow chart of a third method of delivering electroporation, in accordance with some embodiments provided herein.

Referring to FIG. 4, another example method 400 of delivering electroporation can include delivering sub-threshold pulses to the heart at 402, detecting signal summation at 404, increasing pulse intensity at 406, delivering a pulse at 408, determining if signal summation is detected at 410, and delivering therapeutic stimulation at 412.

As described above, delivering sub-threshold pulses to the heart at 402 can be substantially similar to delivering sub-threshold pulses to the heart at 302. For example, delivering sub-threshold pulses can include delivering stimulation below a therapeutic threshold throughout a cardiac cycle. In some cases, sub-threshold stimulation can be delivered as a plurality of pulses. Sub-threshold stimulation can be delivered with a voltage of about 10 microvolts to about 100 microvolts. The sub-threshold stimulation can be delivered between two electrodes of the lead (e.g., electrodes 1 and 3). When the cardiac cycle is in the refractory period, this sub-threshold stimulation will have little effect on the cardiac signals measured in the electrogram. However, when sub-threshold stimulation is delivered in the relative refractory period, there may be small changes seen in the cardiac signal.

In addition, delivering sub-threshold stimulation during the vulnerable period, a summation can be seen in the cardiac signal measured on the electrogram. Detecting signal summation at 404 can identify the vulnerable period of a cardiac cycle. In some cases, the cardiac signal can be measured between two electrodes (e.g., electrodes 2 and 4). In some cases, multiple electrograms can be measured, as described in FIG. 2, and compared to determine a more accurate electrogram. By identifying the vulnerable period, therapy can be delivered to avoid the vulnerable period. This can increase safety and efficacy. Further, while this summation does not reach a threshold to induce ventricular fibrillation, the sub-threshold stimulation may affect the vulnerable period. In some cases, because of the partial depolarization occurring during the repolarization, it can be harder to reach the threshold that induces ventricular fibrillation.

Since the threshold that induces ventricular fibrillation can be harder to reach, the pulse intensity can be increased at 406 and the pulse with increased intensity can be delivered at 408. This pulse can be delivered right after the sub-threshold pulse delivered at 402. In some cases, the pulse intensity can be increased by a percentage (e.g., 125-150%) of the pulse delivered at 402. In some cases, the intensity can be increased by increasing a pulse width, a voltage, or other parameter of the pulse. Upon delivering the pulse with a higher intensity, the electrograms can be measure and analyzed to determine if signal summation is detected at 410. In some cases, the cardiac signal can be measured between two electrodes (e.g., electrodes 2 and 4). In some cases, multiple electrograms can be measured, as described in FIG. 2, and compared to determine a more accurate electrogram. If signal summation is detected at 410, the vulnerable period is still present in the cardiac cycle. Accordingly, the sub-threshold stimulation pulse can be increased in intensity and delivered again at 406 and 408. This process can be repeated until no summation is detected, causing a plateau in summation of the electrogram signal. If no summation is detected at 410, the tissue can be considered in a refractory period, instead of the vulnerable period. Accordingly, therapeutic stimulation can be delivered at 412.

Delivering therapeutic stimulation at 412 can include delivering supra-threshold pulses to the heart. By converting the vulnerable period to a refractory period, therapeutic stimulation to substantially all of a cardiac cycle (e.g., 98-100% of the cardiac cycle). Supra-threshold pulses can have a pulse width (e.g., 100 ns-3 ms). In some cases, the supra-threshold pulses can have varying pulse widths. Supra-threshold pulses can have an amplitude of 1 V to 4 KV. By delivering the supra-threshold pulses for a greater portion of the cardiac cycle, the length of the overall procedure can be reduced. In some cases, the electroporation procedure can take 350-400 ms.

In some cases, the methods described herein can be used to diagnose abnormal arrhythmias. For example, some patients have abnormally long repolarization periods (vulnerable periods), and are therefore more prone to fatal ventricular fibrillation. By determining patients that are more prone to ventricular fibrillation, these patients can receive defibrillators. When detecting abnormal arrhythmias, method 400 can be used to cause a plateau in signal summation. When causing a plateau, the number of pulse increases that are needed to cause the plateau can be related to the length of vulnerable period. For example, if a patient needs 10 pulse increases, as compared to 2 pulse increases, the patient can be considered to have a longer vulnerability period, and accordingly be at a higher risk for ventricular fibrillation. In some cases, once the plateau is reached, the vulnerability period may be decreased. In some cases, the lead can be implanted in the heart for an extended period of time, such that the vulnerable period can be continuously, periodically, or monitored at a varying time interval. When an increase in vulnerable period is detected (e.g., an increase or summated potential seen), electroporation can be delivered to decrease the chances of ventricular fibrillation.

In some cases, the methods described herein can be used in locations other than the heart. For example, the methods can be used in area with electrical signals, such as the brain, nerves, GI tract, etc. In some cases, these methods can be built into a specific device. In some cases, these methods can be implemented in series with currently available devices. In some cases, leads and electrodes can be left in the body to continuously monitor various electrical activity. In some cases, the devices can monitor and provide stimulation to prevent ventricular fibrillation, seizures, fainting, etc.

In some cases, a device that implements the methods described herein can include insulated ports for each electrode, so electrodes can be analyzed and filtered separately. In some cases, each pole has a separate pole, which are kept insulated from each other. In some cases, an omnipolar delivery system can be used to implement the methods described herein. In some cases, the methods described herein can be implemented using a device that is capable of delivery energy solely after a QRS complex to improve the device. For example, the methods herein can be implemented such that before delivery of stimulation, the device goes through one or more of the methods. In some cases, surgery can be dangerous for patients, due to devices needing to be turned off. In some cases, the devices that implement the methods described herein do not need to be turned off during surgery.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures does not necessarily require the particular order shown, or sequential order, to achieve desirable results. In certain implementations, multitasking and parallel processing may be advantageous.

What is claimed is:

1. A method of triggering electroporation, the method comprising:
    inserting a lead in or around a heart of a patient, the lead comprising a first electrode, a second electrode, and a third electrode that are both sensing and delivering electrodes;
    delivering electroporation stimulation to the heart below a threshold during a cardiac cycle of the patient;
    measuring a first electrocardiogram between the first and second electrodes of the lead;
    measuring a second electrocardiogram between the first and third electrodes of the lead;
    comparing the first and second electrocardiograms;
    identifying signals common to the first and second electrocardiograms;
    removing the signals common to the first and second electrocardiograms, thereby creating a modified electrocardiogram;
    determining whether the modified electrocardiogram comprises a cardiac signal;
    identifying a vulnerable period in the cardiac cycle by detecting a signal summation in the cardiac signal; and
    in response to: i) determining that the modified electrocardiogram comprises the cardiac signal, and ii) identifying the vulnerable period of the cardiac cycle, delivering electroporation stimulation above the threshold to the heart during the cardiac cycle except during the vulnerable period by using at least one of the first, second, and third electrodes after the cardiac signal is determined,
    wherein the threshold comprises a voltage of about 10 microvolts to about 100 microvolts.

2. The method of claim 1, wherein a distance between the first electrode and the third electrode is greater than a distance between the first electrode and the second electrode.

3. The method of claim 1, wherein the first and second electrodes are located linearly along the lead.

4. The method of claim 1, wherein the first and third electrodes are located linearly along the lead.

5. The method of claim 1, wherein a filter is used to remove the signals common to the first and second electrocardiograms.

6. The method of claim 5, wherein the filter is a common mode rejection filter.

7. The method of claim 1, wherein the delivering electroporation stimulation to the heart below the threshold during the cardiac cycle of the patient comprises:
    delivering a first set of stimulation pulses for the cardiac cycle, wherein the first set of stimulation pulses has a first intensity below the threshold; and
    delivering a third set of stimulation pulses for the cardiac cycle, wherein the third set of stimulation pulses has a third intensity between the first intensity and the threshold; and
    wherein the delivering electroporation stimulation to the heart above the threshold during the cardiac cycle of the patient comprises:
    delivering a second set of stimulation pulses for the cardiac cycle, wherein the second set of stimulation pulses has a second intensity above the threshold; and
    delivering a fourth set of stimulation pulses for the cardiac cycle when the signal summation is not detected, wherein the fourth set of stimulation pulses has a fourth intensity above the threshold.

8. The method of claim 7, wherein the signal summation is indicative of the vulnerable period of the cardiac cycle.

9. The method of claim 1, wherein delivering electroporation stimulation above the threshold to the heart during the cardiac cycle except during the vulnerable period decreases a risk of generating an unwanted arrhythmia or an unwanted ventricular fibrillation.

10. The method of claim 1, wherein delivering electroporation stimulation above the threshold to the heart during the cardiac cycle except during the vulnerable period comprises delivering supra-threshold pulses to the heart, the supra-threshold pulses comprising a pulse width of about 100 nanoseconds (ns) to about 3 milliseconds (ms) and an amplitude of about 1 volt to about 4 kilovolts.

11. A device for delivering electroporation, the device comprising:
a lead comprising a first electrode, a second electrode, and a third electrode that are both sensing and delivering electrodes;
a memory that is capable of storing computer executable instructions; and
a processor that is configured to facilitate execution of the executable instructions stored in memory, wherein the instructions configure the processor to:
deliver electroporation stimulation to a heart of a patient below a threshold during a cardiac cycle;
measure cardiac signals from at least one of the first, second, and third electrodes on the lead, wherein the measuring of cardiac signals comprises:
measuring a first electrocardiogram between the first and second electrodes;
measuring a second electrocardiogram between the first and third electrodes;
comparing the first and second electrocardiograms;
identifying signals common to the first and second electrocardiograms;
removing signals common to the first and second electrocardiograms, thereby creating a modified electrocardiogram; and
determining whether the modified electrocardiogram comprises a cardiac signal;
identify a vulnerable period in the cardiac cycle by detecting a signal summation in the cardiac signal; and
in response to: (i) determining that the modified electrocardiogram comprises the cardiac signal, and (ii) identifying the vulnerable period of the cardiac cycle, deliver electroporation stimulation above the threshold to the heart during the cardiac cycle except during the vulnerable period by using at least one of the first, second, and third electrodes after the cardiac signal is determined,
wherein the delivery of electroporation stimulation to the heart below the threshold during the cardiac cycle of the patient comprises:
delivering a first set of stimulation pulses for the cardiac cycle, wherein the first set of stimulation pulses has a first intensity below the threshold; and
delivering a third set of stimulation pulses for the cardiac cycle, wherein the third set of stimulation pulses has a third intensity between the first intensity and the threshold, and
wherein the delivery of electroporation stimulation to the heart above the threshold during the cardiac cycle of the patient comprises:
delivering a second set of stimulation pulses for the cardiac cycle, wherein the second set of stimulation pulses has a second intensity above the threshold; and
delivering a fourth set of stimulation pulses for the cardiac cycle when the signal summation is not detected, wherein the fourth set of stimulation pulses has a fourth intensity above the threshold, and wherein the threshold comprises a voltage of about 10 microvolts to about 100 microvolts.

12. The device of claim 11, wherein the electrodes are positioned linearly along a length of the lead, and wherein a distance between the first electrode and the third electrode is greater than a distance between the first electrode and the second electrode.

13. The device of claim 11, wherein a filter is used to remove the signals common to the first and second electrocardiograms.

14. The device of claim 13, wherein the filter is a common mode rejection filter.

15. The device of claim 11, wherein delivering electroporation stimulation above the threshold to the heart during the cardiac cycle except during the vulnerable period decreases a risk of generating an unwanted arrhythmia or an unwanted ventricular fibrillation.

16. The device of claim 11, wherein delivering electroporation stimulation above the threshold to the heart during the cardiac cycle except during the vulnerable period comprises delivering supra-threshold pulses to the heart, the supra-threshold pulses comprising a pulse width of about 100 ns to about 3 ms and an amplitude of about 1 volt to about 4 kilovolts.

17. A device for delivering electroporation, the device comprising:
a lead comprising a first electrode, a second electrode, and a third electrode that are both sensing and delivering electrodes;
a memory that is capable of storing computer executable instructions; and
a processor that is configured to facilitate execution of the executable instructions stored in memory, wherein the instructions configure the processor to:
deliver electroporation stimulation to a heart of a patient below a threshold during a cardiac cycle;
measure cardiac signals from at least one of the first, second, and third electrodes on the lead, wherein the measuring of cardiac signals comprises:
measuring a first electrocardiogram between the first and second electrodes;
measuring a second electrocardiogram between the first and third electrodes;
comparing the first and second electrocardiograms;
identifying signals common to the first and second electrocardiograms;
removing signals common to the first and second electrocardiograms, thereby creating a modified electrocardiogram; and
determining whether the modified electrocardiogram comprises a cardiac signal;
identify a vulnerable period in the cardiac cycle by detecting a signal summation in the cardiac signal; and
in response to: (i) determining that the modified electrocardiogram comprises the cardiac signal, and (ii) identifying the vulnerable period of the cardiac cycle, deliver electroporation stimulation above the threshold to the heart during the cardiac cycle except during the vulnerable period by using at least one of the first, second, and third electrodes after the cardiac signal is determined,
wherein delivering electroporation stimulation above the threshold to the heart during the cardiac cycle except during the vulnerable period decreases a risk of generating an unwanted arrhythmia or an unwanted ventricular fibrillation.

18. A device for delivering electroporation, the device comprising:
- a lead comprising a first electrode, a second electrode, and a third electrode that are both sensing and delivering electrodes;
- a memory that is capable of storing computer executable instructions; and
- a processor that is configured to facilitate execution of the executable instructions stored in memory, wherein the instructions configure the processor to:
  - deliver electroporation stimulation to a heart of a patient below a threshold during a cardiac cycle;
  - measure cardiac signals from at least one of the first, second, and third electrodes on the lead, wherein the measuring of cardiac signals comprises:
    - measuring a first electrocardiogram between the first and second electrodes;
    - measuring a second electrocardiogram between the first and third electrodes;
    - comparing the first and second electrocardiograms;
    - identifying signals common to the first and second electrocardiograms;
    - removing signals common to the first and second electrocardiograms, thereby creating a modified electrocardiogram; and
    - determining whether the modified electrocardiogram comprises a cardiac signal;
  - identify a vulnerable period in the cardiac cycle by detecting a signal summation in the cardiac signal; and
  - in response to: (i) determining that the modified electrocardiogram comprises the cardiac signal, and (ii) identifying the vulnerable period of the cardiac cycle, deliver electroporation stimulation above the threshold to the heart during the cardiac cycle except during the vulnerable period by using at least one of the first, second, and third electrodes after the cardiac signal is determined,
- wherein delivering electroporation stimulation above the threshold to the heart during the cardiac cycle except during the vulnerable period comprises delivering supra-threshold pulses to the heart, the supra-threshold pulses comprising a pulse width of about 100 ns to about 3 ms and an amplitude of about 1 volt to about 4 kilovolts.

19. A device for delivering electroporation, the device comprising:
- a lead comprising a first electrode, a second electrode, and a third electrode that are both sensing and delivering electrodes;
- a memory that is capable of storing computer executable instructions; and
- a processor that is configured to facilitate execution of the executable instructions stored in memory, wherein the instructions configure the processor to:
  - deliver electroporation stimulation to a heart of a patient below a threshold during a cardiac cycle;
  - measure cardiac signals from at least one of the first, second, and third electrodes on the lead, wherein the measuring of cardiac signals comprises:
    - measuring a first electrocardiogram between the first and second electrodes;
    - measuring a second electrocardiogram between the first and third electrodes;
    - comparing the first and second electrocardiograms;
    - identifying signals common to the first and second electrocardiograms;
    - removing signals common to the first and second electrocardiograms, thereby creating a modified electrocardiogram; and
    - determining whether the modified electrocardiogram comprises a cardiac signal;
  - identify a vulnerable period in the cardiac cycle by detecting a signal summation in the cardiac signal; and
  - in response to: (i) determining that the modified electrocardiogram comprises the cardiac signal, and (ii) identifying the vulnerable period of the cardiac cycle, deliver electroporation stimulation above the threshold to the heart during the cardiac cycle except during the vulnerable period by using at least one of the first, second, and third electrodes after the cardiac signal is determined,
- wherein the threshold comprises a voltage of about 10 microvolts to about 100 microvolts.

\* \* \* \* \*